United States Patent
Hedberg

(10) Patent No.: US 10,544,387 B2
(45) Date of Patent: Jan. 28, 2020

(54) BIOREACTORS AND USES THEREOF

(71) Applicant: Biostage, Inc., Holliston, MA (US)

(72) Inventor: Herbert Hedberg, Holliston, MA (US)

(73) Assignee: Biostage, Inc., Holliston, MA (US)

( * ) Notice: Subject to any disclaimer, the term of this patent is extended or adjusted under 35 U.S.C. 154(b) by 0 days.

(21) Appl. No.: 14/780,692

(22) PCT Filed: Mar. 27, 2014

(86) PCT No.: PCT/US2014/032025
§ 371 (c)(1),
(2) Date: Sep. 28, 2015

(87) PCT Pub. No.: WO2014/160869
PCT Pub. Date: Oct. 2, 2014

(65) Prior Publication Data
US 2016/0053213 A1    Feb. 25, 2016

Related U.S. Application Data

(60) Provisional application No. 61/805,909, filed on Mar. 27, 2013.

(51) Int. Cl.
C12M 3/00    (2006.01)
C12M 1/00    (2006.01)
C12M 1/12    (2006.01)
C12M 1/34    (2006.01)

(52) U.S. Cl.
CPC .......... *C12M 21/08* (2013.01); *C12M 23/38* (2013.01); *C12M 25/00* (2013.01); *C12M 41/00* (2013.01)

(58) Field of Classification Search
CPC ...... C12M 23/08; C12M 23/38; C12M 41/00; C12M 21/08; C12M 25/00; C12M 29/20
See application file for complete search history.

(56) References Cited

U.S. PATENT DOCUMENTS

| | | | |
|---|---|---|---|
| 5,689,961 A * | 11/1997 | Cosman | A01N 1/02 62/373 |
| 2008/0113426 A1 | 5/2008 | Smith et al. | |
| 2009/0104640 A1* | 4/2009 | Barron et al. | G01N 33/5082 435/29 |
| 2011/0033918 A1 | 2/2011 | Asnaghi et al. | |
| 2013/0109007 A1* | 5/2013 | Akra et al. | C12M 21/08 435/3 |

* cited by examiner

*Primary Examiner* — Gautam Prakash

(57) ABSTRACT

Aspects of the disclosure relate to bioreactors for maintaining biological objects (e.g., organ or engineered tissues) under culture conditions. In some embodiments, bioreactors and cover assemblies are provided that comprise a support base for supporting a biological object. In some embodiments, bioreactors and cover assemblies are provided that comprise a movable support base configured such that a user can manipulate its position and thus the relative position of the biological object.

10 Claims, 8 Drawing Sheets

BIOREACTORS AND USES THEREOF

BACKGROUND

This is a United States National stage entry which claims the benefit of PCT/US2014/32025 filed Mar. 27, 2014 which application claims the benefit of U.S. Provisional Patent Application Ser. No. 61/805,909, filed Mar. 27, 2013 entitled "BIOREACTORS AND USES THEREOF," the contents of which are incorporated herein by reference in their entirety.

A goal in the field of tissue and organ regeneration is to be able to grow body parts that can be used for transplantation into individuals in order to treat different medical conditions that are associated with organ or tissue disease, aging, failure, and/or injury. The growth of artificial organs and tissues in vitro has been studied for many years. Significant progress has been made in the research context towards an understanding of the biological and physiological processes that are associated with the regeneration of tissues and organs from cellular preparations. Examples of several basic organ models or partial organs have been cultured in vitro, including models of lung and liver, using bioreactors. Bioreactors have also been used to culture and study organs obtained from a subject or cadaver ex vivo.

SUMMARY

Provided herein are reactors useful for culturing, cellularizing, decellularizing, and/or conditioning biological or synthetic objects, such as tissues or organs (e.g., engineered tissues or organs). In some embodiments, the bioreactors are particularly useful for culturing large organs such as lungs or hearts. According to some aspects of the disclosure, a bioreactor is provided that comprises a vessel having a chamber and at least one opening that communicates with the chamber. In some embodiments, the bioreactor comprises a cover component that is configured for covering the at least one opening. In some embodiments the chamber of the bioreactor vessel is configured for containing a biological object under culture conditions (e.g., sterile culture conditions). In some embodiments, a support structure is attached to the cover component, the support structure being configured for supporting the biological object when the cover component is separated from the vessel and/or for positioning the biological object within the chamber when the cover component is joined with the vessel to cover the at least one opening. In some embodiments, presence of the support structure enables a user (e.g., a single person) to readily position the biological object in the bioreactor without having to access the internal chamber of the vessel. The user, in some embodiments, can place the biological object on a support base of the support structure when the cover assembly is separated from the vessel. Subsequently, the user may pass the support structure through the opening of the vessel, positioning the support base (and thus, the biological object) into the vessel chamber as the cover assembly is joined with the vessel to cover the opening of the vessel. This arrangement is advantageous, in some embodiments, because it facilitates maintenance of the sterility of the vessel because it minimizes the likelihood that a user will contact the internals of the vessel with unsterile objects while positioning the biological object (e.g., organ or engineered tissue) inside the vessel chamber. This arrangement, in some embodiments, also enables a single user to assemble the bioreactor and position the biological object in the bioreactor.

In some embodiments, a bioreactor is provided that comprises at least one port in the cover component. In some embodiments, the at least one port is configured for providing access to the chamber while the cover component is joined with the vessel to cover the at least one opening. The port may have any suitable size or shape. The port may be rounded or rectangular. The port may be configured for mating with one or more fluidic connections. In some embodiments, the port is connected with one or more fluid conduits configured for supplying or returning a perfusion fluid to or from the biological object. In some embodiments, the port is connected with a bubble trap configured for remove entrained air from a perfusion line to eliminate the generation of air pockets in a biological object through which a perfusion fluid is passed. In some embodiments, a bioreactor is provided that comprises a first fluid conduit attached to the at least one port such that the first fluid conduit is disposed in the chamber when the cover component is joined with the vessel to cover the at least one opening. In some embodiments of the bioreactor, the first fluid conduit is configured for attachment to a second fluid conduit of the biological object. In some embodiments of the bioreactor, the first fluid conduit is configured for attachment to a second fluid conduit of the biological object through the use of one or more sutures. In some embodiments, the biological object is lung, and the biological conduit is an airway passage, optionally which is a trachea or bronchial tube. In some embodiments, the biological object is a heart, and the biological conduit is a ventricle or aorta. In some embodiments, the biological object is a liver, and the biological conduit is a hepatic portal vein.

In some embodiments of the bioreactor, a support structure is provided that comprises a support base (e.g., a platform, sling, or hammock-like structure) for supporting the biological object and one or more attachment components that attach the support base to the cover component. In some embodiments of the bioreactor, the support structure comprises an adjustment component for adjusting the position of the support base relative to the chamber when the cover component is joined with the vessel to cover the at least one opening. In some embodiments of the bioreactor, one or more attachment components comprise at least one elongate member having a first end attached to the support base, a body portion passing through an opening in the cover component, and a second end disposed on the side of the cover component that is external to the chamber when the cover component is joined with the vessel to cover the at least one opening. In some embodiments, the elongate member is configured to be manipulated externally from the bioreactor chamber to control the relative position of the support base within the bioreactor. The elongate members may be manipulated by translational (See, e.g., FIG. 1) or rotational motion (See, e.g., FIG. 8) to control the position of the support base in the vessel chamber. In some embodiments, the support base is positioned (e.g., by manipulating the elongate members) such that it suspends the biological object in the vessel chamber. In some embodiments the support base is lowered such that it is in contact with an internal surface of the vessel chamber, e.g., so that the biological object is not suspended by the support base in the vessel chamber.

In some embodiments of a bioreactor, the support base is a movable support base configured such that a user can manipulate its position relative to the chamber when the cover component is joined with the vessel to cover the at least one opening.

In some embodiments of the bioreactor, the support base has a surface for supporting the biological object that, when the cover component is joined with the vessel to cover the at least one opening, is positioned along an axis substantially parallel to the opening of the vessel. In other embodiments of the bioreactor, the support base has a surface for supporting the biological object that, when the cover component is joined with the vessel to cover the at least one opening, is positioned along an axis substantially perpendicular to the opening of the vessel.

In some embodiments of the bioreactor, the vessel, cover component and/or support structure is composed of material(s) that can sustain temperatures within a range of 120° C. to 150° C. (e.g., for up to 30 minutes, up to 60 minutes, or more) without substantial deterioration of structure or function. In some embodiments of the bioreactor, the vessel, cover component and/or support structure is composed of autoclavable material(s). In some embodiments of the bioreactor, the chamber is configured for containing a biological object under sterile culture conditions.

In some embodiments of the bioreactor, a vessel comprises a surface circumscribing the at least one opening that is configured to interface with a surface of the cover component when the cover component is joined with the vessel to cover the at least one opening. In some embodiments of the bioreactor, one or more fasteners (e.g., bolts, screws, clamps) are provided for joining the cover component with the vessel. In some embodiments of the bioreactor, the cover component is joined with the vessel without the use of fasteners. For example, in some embodiments where the bioreactor is in vertical configuration, the cover component may be joined with the vessel through its own weight without the use of fasteners. In some embodiments, the cover component may be joined with the vessel using an adhesive material.

In some aspects, a bioreactor is provided that comprises a vessel having a chamber and at least one opening that communicates with the chamber, the chamber being configured for containing a biological object under culture conditions. In some embodiments the bioreactor further comprises a cover component configured for covering the at least one opening, wherein the cover component is joined with the vessel to cover the at least one opening. In some embodiments, bioreactor further comprises a support structure attached to the cover component. In some embodiments, the support structure comprises a movable support base for supporting the biological object. In some embodiments, the movable support base is configured such that a user can manipulate its position relative to the chamber when the cover component is joined with the vessel to cover the at least one opening. In some embodiments, the biological object positioned within the chamber. In some embodiments, the biological object is suspended in the chamber by the support base. In some embodiments, the bioreactor further comprises at least one port provided in the cover component; and a first fluid conduit attached to the at least one port such that the first fluid conduit is disposed in the chamber, wherein the first fluid conduit is configured for attachment to a second fluid conduit of the biological object. In some embodiments, the first fluid conduit is attached to the second fluid conduit of the biological object.

According to some aspects of the disclosure, cover assemblies for bioreactors are provided. In some embodiments, a cover assembly comprises a cover component having a surface for interfacing with a vessel of the bioreactor to cover an opening of the vessel, the opening being configured to permit entry of a biological object into the bioreactor; and a support structure attached to the cover component, the support structure comprising a support base for supporting the biological object and one or more attachment components that attach the support base to the cover component. In some embodiments, the support base is a movable support base configured such that a user can manipulate its position relative to the cover component. In some embodiments, the one or more attachment components comprise at least one elongate member having a first end attached to the support base, a body portion passing through an opening in the cover component, and a second end disposed on the opposite side of the cover component as the support base. In some embodiments, the support base has a surface for supporting the biological object that is substantially perpendicular to a cover surface of the cover component. In some embodiments, the support base has a surface for supporting the biological object that is substantially parallel to a cover surface of the cover component. In some embodiments, the support structure further comprises an adjustment component for adjusting the position of the support base relative to the cover component. In some embodiments, the cover assembly further comprises at least one port provided in the cover component. In some embodiments, the cover assembly further comprises a first fluid conduit attached to the at least one port such that the first fluid conduit is disposed in the chamber when the cover component is joined with the vessel to cover the at least one opening. In some embodiments, the first fluid conduit is configured for attachment to a second fluid conduit of the biological object, optionally through the use of one or more sutures. In some embodiments, the cover component and/or support structure is composed of material(s) that can sustain temperatures within a range of 120° C. to 150° C. (e.g., for a period of up to 30 minutes, 60 minutes, 2 hours or more) without a substantial deterioration in structure or intended function. In some embodiments, the cover component and/or support structure is composed of autoclavable material(s).

BRIEF DESCRIPTION OF DRAWINGS

The accompanying drawings are not intended to be drawn to scale. For purposes of clarity, not every component may be labeled in every drawing. In the drawings.

DETAILED DESCRIPTION

Figure 1:
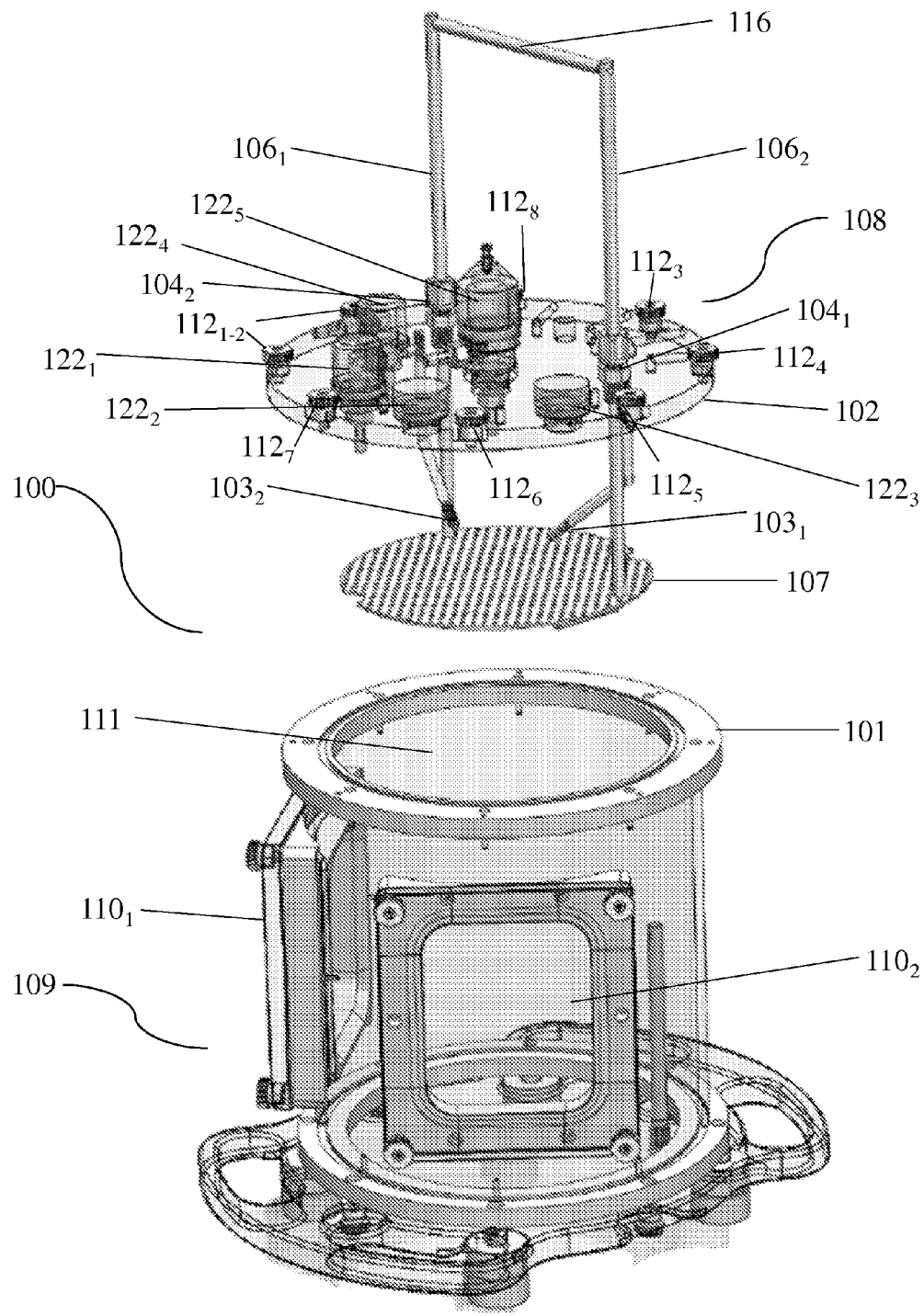
FIG. 1 depicts a bioreactor (100) comprising a vessel (109) and a vertically arranged cover assembly (108), including a support structure for supporting a biological object (e.g., an organ)

According to some aspects of the disclosure the bioreactors provided herein are useful for maintaining biological objects under culture conditions. As used herein, the term "biological object" refers to an object comprising a biologically compatible substrate suitable for culturing cells. In some embodiments, a biological object is an organ, such as a lung, heart or liver. Other examples of suitable organs are disclosed herein. In some embodiments, the biological object is a decellularized organ or tissue. In some embodiments, the biological object comprises an engineered tissue or organ. Other suitable biological objects are disclosed herein.

Bioreactors may include a vessel comprising a chamber and at least one opening to the chamber. The chamber may have any suitable size and/or shape. In some embodiments, the chamber is configured for monitoring and/or modulating the growth conditions within the chamber. In some embodiments, the chamber is configured for directly monitoring the conditions of the cells or substitute tissue or organ within the chamber, or for monitoring the conditions of the chamber itself, or for a combination thereof.

Non-limiting examples of bioreactors and components of such bioreactors are provided in FIGS. 1-8. It should be appreciated that in some embodiments, aspects of the disclosure relate to a complete bioreactor (e.g., as illustrated in the Figures and Examples) and related systems (e.g., associated pumps, reservoirs, supports, each of which may be physically and functionally connected to, associated with, or joined to a reactor vessel or other component). However, in some embodiments, the disclosure provides one or more of the component parts, or kits including such component parts. For example, embodiments of the disclosure may be a vessel, a cover assembly, a support structure, a support structure that can be isolated from the cover assembly, and any one or more of the component parts (e.g., as illustrated by the non-limiting examples of component parts described and shown in the Figures and Examples), and kits including such component parts.

It should be appreciated that the bioreactor can be a single piece or multiple piece device (e.g., a vessel with a single lid that can be removed or opened, a vessel with a top and a bottom lid, either one or both of which can be removed or opened, a vessel with one or more covers that can be removed or opened for example to access the inside of the vessel chamber, or any other configuration or combination thereof, for example, wherein the vessel can be cylindrical or any other shape). An example of a bioreactor is comprised of a vessel with an opening, windows, and a cover assembly interface. In some embodiments, a cover assembly may be joined with the vessel to cover an opening of the vessel. In some embodiments, the cover assembly comprises a support structure having elongate members passing through a cover component that are connected to a support base for supporting a biological object. In some embodiments, fasteners (e.g., clamps, bolts) may be used to releasably secure the elongate members to the cover component, e.g., to lock the elongate members in place. In some embodiments, the assembly provides one or more adjustment components that enable a user to control position of the elongate members and thus the position of the support base within the vessel chamber. In some embodiments, an optional crossbar or other component(s) may be used to join multiple elongate members.

In some embodiments, the support base is fully adjustable in different directions but can be held in place (e.g., with a lock, or stop, clamp, pin, or other suitable mechanical feature) so that a organ/tissue or other object on the support base can be held in place while connections are made (and then lowered or placed into the vessel). In some embodiments, the support base includes features that allow a single person to readily operate it. For example, the height or position of the support base may be readily adjustable using any suitable method including, for example, mechanical or electromechanical devices, such as, winches, pulleys, wheels, cogs, or cranks. In some embodiments, a motorized system may be used to maneuver and control support base position.

It should be appreciated that bioreactors can be made of any suitable material (including a printed material from a 3D printer). Bioreactors may be made of transparent or translucent materials. Examples of suitable materials for bioreactors are glass or plastics such as polymethyl methacrylate (PLEXIGLAS), polyesters such as PET, polycarbonate, polyamide, polystyrene, polyethylene, polypropylene, polyvinyl chloride. Laminates can also be used, which comprise a composite of an addition-crosslinked silicone molding and a glass or plastic molding. In some embodiments, all of the material of the bioreactor (including the wall, connectors, screws, clips, supply lines, feed lines, outlet lines, valves, bubble traps, etc.) are made of an MRI compatible (e.g., non-metallic, non-magnetic or non-paramagnetic) material.

It should be appreciated that the support base can be composed of a multitude of suitable materials. Exemplary materials include, KEVLAR, polycarbonate and stainless steel. For example, the support base could be composed of porous or non-porous membrane or a perforated support layer, a biodegradable or dissolvable support layer. The support base may have one or more supporting layers that are impregnated with a biocatalyst (e.g., enzymes or other substances that are preferable to release close to the cell culture or organ). Generally materials are chosen that can be autoclaved and/or MRI compatible.

The support base inside the vessel may either stay in place supporting the biological object, or it may be lowered to bottom of the chamber, which may be desirable, for example, if the chamber is filled with media and the supported substrate approximates neutral buoyancy.

The cover component may contain a plurality of ports (e.g., supports various options including locking mechanisms, plugs, bubble traps, right angle); and holes (e.g., for fastening cover assembly to vessel). Ports may contain O-rings, for example. Fluid conduits (e.g., cannula, drain etc.) are attached to and transverse ports and are shown in configuration for attachment to a biological object.

Cover components (lids, bases) and sides of bioreactor can include one or more ports (e.g., for catheters, wires, hosing, or other components) that allow components to be connected to the interior of the device. In some embodiments, ports and components associated with them are MRI compatible. In some embodiments, ports are sealed (e.g., using a cap) when not in use. In some embodiments, ports are configured with a sealed or self-sealing conduit or orifice, configured such that a wire, hose, tube, catheter, etc. can be introduced into the chamber/vessel in a sterile fashion through the ports.

A non-limiting example of a bioreactor (100) is depicted in FIG. 1, which is comprised of a vessel (109) with an opening (111), windows, and a cover assembly interface (101). A cover assembly (108; top) is joined with the vessel (109; bottom) to cover the opening (111) of the vessel (109).

The cover assembly (108) depicted has elongate members (1061-2) passing though the cover component (102). In some embodiments, such as depict in FIG. 1, fasteners (e.g. clamps, bolts) (1041-2) may be provided for releasably locking the elongate members (1061-2) in place. An optional crossbar (116) may be used to join the elongate members (1061-2), e.g., at an end external from the bioreactor. In FIG. 1, two elongate members (1061-2) are depicted running substantially parallel to one another and substantially perpendicular to a support base (107) (e.g., a platform or hammock like structure configured for supporting the biological object). Elongate members (1061-2) may be connected to the support base (107) using any appropriate method (e.g., fasteners (e.g., screws, nuts and bolts), welds, adhesive bonding)

In the configuration depicted by FIG. 1, a support base (107) is variably positioned and fastened in place by clamps (1041-2). The cover component (102) contains a plurality of ports (1051-5). Such ports may be interconnected with various port-adapted components 1221-5 e.g., locking mechanisms for elongate members, plugs, bubble traps, angled passages for directing fluid flow); and holes (112) (e.g. for fastening the cover assembly to vessel). Fluid conduits (e.g. cannulas, drains etc.) (1031-2) are attached to and pass through ports in the cover component (102) and are shown in a configuration suitable for attachment to a fluid conduit of biological object (e.g., a trachea of a lung or a ventricle or aorta of a heart).

In some embodiments the fluid conduits are connected to conduits of the biological object to perfuse a fluid (e.g., a culture medium) through the biological object.

Port-adapted component (1225) is a bubble trap configured for removing air from the chamber of the bioreactor vessel (109). Any appropriate bubble traps may be used. For example, a suitable bubble trap may comprise a ball valve assembly that permits air to be removed from the bioreactor vessel. It should be appreciated that bubble traps can be provided at multiple positions on a bioreactor to enable removal of air from the bioreactor when the bioreactor is in any of a number of different orientations. For example, a bioreactor may be configured with one or more bubble traps on the top of the bioreactor (e.g., n cover component of a cylindrical bioreactor (e.g., as depicted in FIG. 1)) that function when the bioreactor is top up, and one or more bubble traps on lateral portions(s) of the bioreactor (e.g., the curves sides of a cylindrically shaped bioreactor (e.g., as depicted in FIG. 1)) that function to remove air from the bioreactor vessel when the bioreactor is positioned on its side. In this way, the bioreactor can be rotated or repositioned at various different orientations without trapping air bubbles within the bioreactor vessel.

Figure 2:
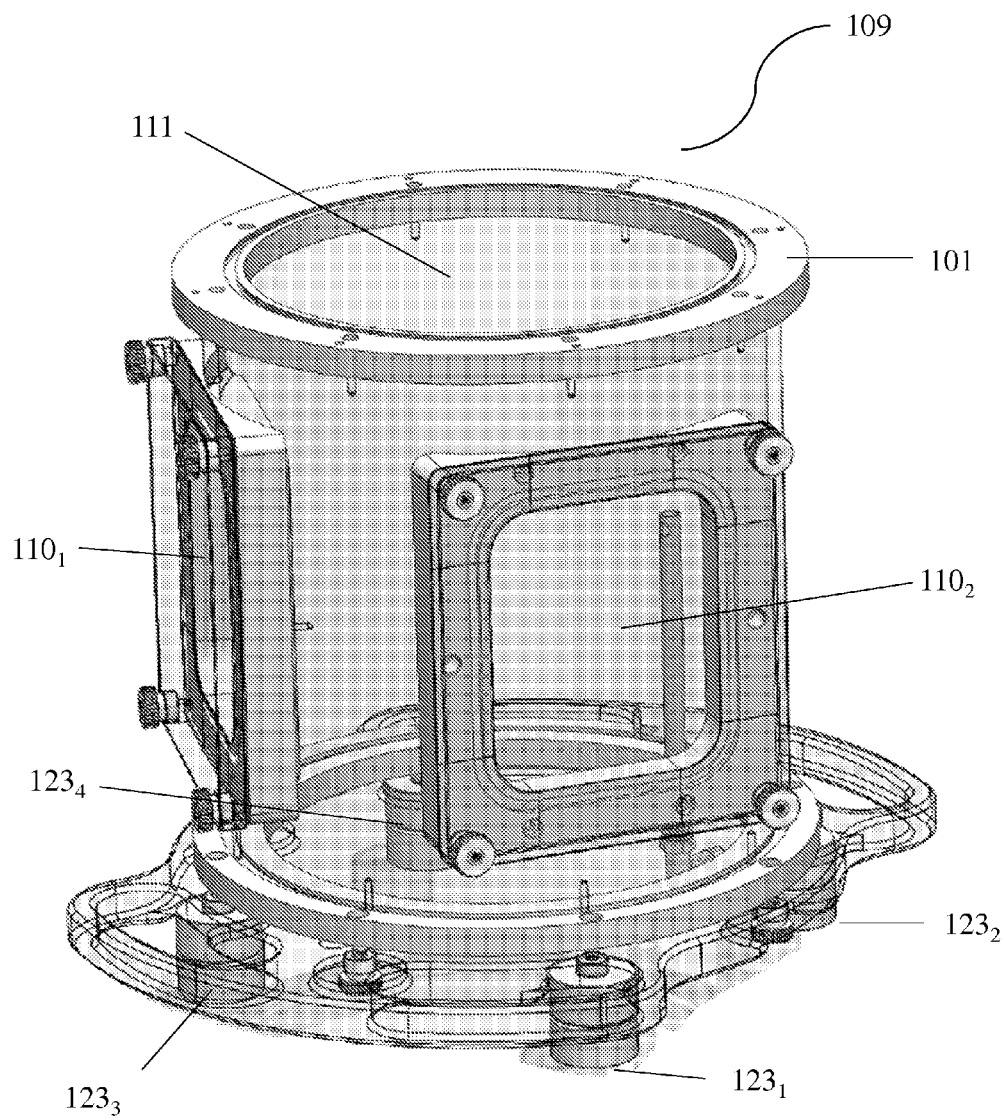
FIG. 2 depicts a vessel (109) of a bioreactor (100)

In some embodiments, a bubble trap (debubbler) comprises a simple venting system (for example available from HUGO SACHS) so that flow of bubbles can enter a space with no moving parts. In some embodiments, this space can be vented to the outside (e.g., via a connection to a tube). Bubble traps can be placed in any plane of the bioreactor (so the bioreactor can be used horizontally or vertically). In some embodiments, the traps or other components are attached to the bioreactor in different planes (in some embodiments they are integral to the walls, lids, covers, and/or bases of one or more bioreactors). Accordingly, in some embodiments, a bioreactor includes one or more ports in different planes into which trap(s) and other components can be inserted. Such components can be connected to the ports via threaded, compression, snap, "turn and twist", "twist and clamp" or other suitable connections. FIG. 2 depicts a vessel (109) for a bioreactor (100) comprised of an opening (111), windows (1101-2), and a cover assembly interface (101).

In some embodiments, protrusions are provided that are positioned externally on a bioreactor vessel and that are configured to distance an external surface of the bioreactor from a contact surface. As illustrated in FIG. 2, protrusions (1231-4) are positioned on the bottom surface of a bioreactor and elevate the bioreactor base off of a horizontal surface. In some embodiments, this configuration enables a user to readily grasp the base of the bioreactor for purposes of maneuvering the bioreactor (e.g., for purposes of raising the bioreactor up off its base). In some embodiments, the bioreactor vessel itself forms one or more protrusions. However, in some embodiments, the one or more protrusions are separate components attached to the bioreactor vessel. In some embodiments, the protrusions (e.g., feet, nipples) can be integral to the wall of the bioreactor. In some embodiments, the size (e.g., height, length) of the protrusions should be sufficient to allow fingers or hands to get under the device or between the device and a contact surface. In some embodiments, the size is sufficient to allow wires or other devices (e.g., a camera) to be placed under the device to connect and/or monitor the inside of the bioreactor. In some embodiments, a transparent object (e.g., a window) of any suitable shape or size is located under the bioreactor (or at any other position(s) within a wall, cover, lid, and/or base of a bioreactor) to allow a camera to monitor the inside of the bioreactor from the outside. In some embodiments a device on the inside (e.g., a wiper, a device having a flexible, edged surface (e.g., a rubber surface), such as a squeegy) is configured to clean the inside surface of the window (e.g., to remove condensation or other material) to avoid interfering with the camera view into the bioreactor. The wiper type device may be motorized, for example, such that it moves or rotates, e.g., in a periodic fashion, to clean the transparent object.

In some embodiments, a bioreactor may be configured with a device for delivering or injecting material (e.g., growth factors, cytokines, cells, etc.) to an organ or tissue being processed within the sterile confines of the bioreactor. In some embodiments, the bioreactor vessel made be pressurized such that it may be opened under positive pressure so that a user can access the bioreactor chamber in a manner that minimizes the likelihood of introducing contaminants into the chamber. In some embodiments, the bioreactor is fitted with a sterile glove assembly such that a user can insert his or her arms through the gloves into the bioreactor in a sterile fashion. In this configuration a sterile injection device may be present within the chamber such that it can be manipulated by the user's hands through the glove assembly for purposes of delivering or injecting material to an organ or tissue being processed within the bioreactor. In some embodiments, the bioreactor is fitted with a wheaton cap or resealable membrane material on a wall, cover or other external plane through which an injection or delivery device can be inserted in a sterile fashion.

In some embodiments, a delivery device or injector is positioned along a bioreactor wall (out of the way when not in use) for long term needle placement when delivering material to a tissue or organ via a syringe pump or other device. In some embodiments, a connecting tube, which may be composed of stainless steel or another suitable material, may be positioned through the bioreactor wall and configured for penetrating a tissue or organ housed in the bioreactor. The tube may be configured with an injection needle positioned within the tissue or organ. Flow of material through the tube may be controlled or manipulated from outside of the bioreactor via a syringe like device, pump or other suitable fluid transfer device. In some embodiments, the tube is locked into position in the bioreactor wall, e.g., via a jam nut that is threaded into a port (e.g., a machined, V-bottomed hole) in a bioreactor wall or cover component such that the nut compresses two ball halves and ferrules together to lock the tube in position. In such embodiments, a rigid, tight seal is formed when the jam nut is tightened.

Figure 3:
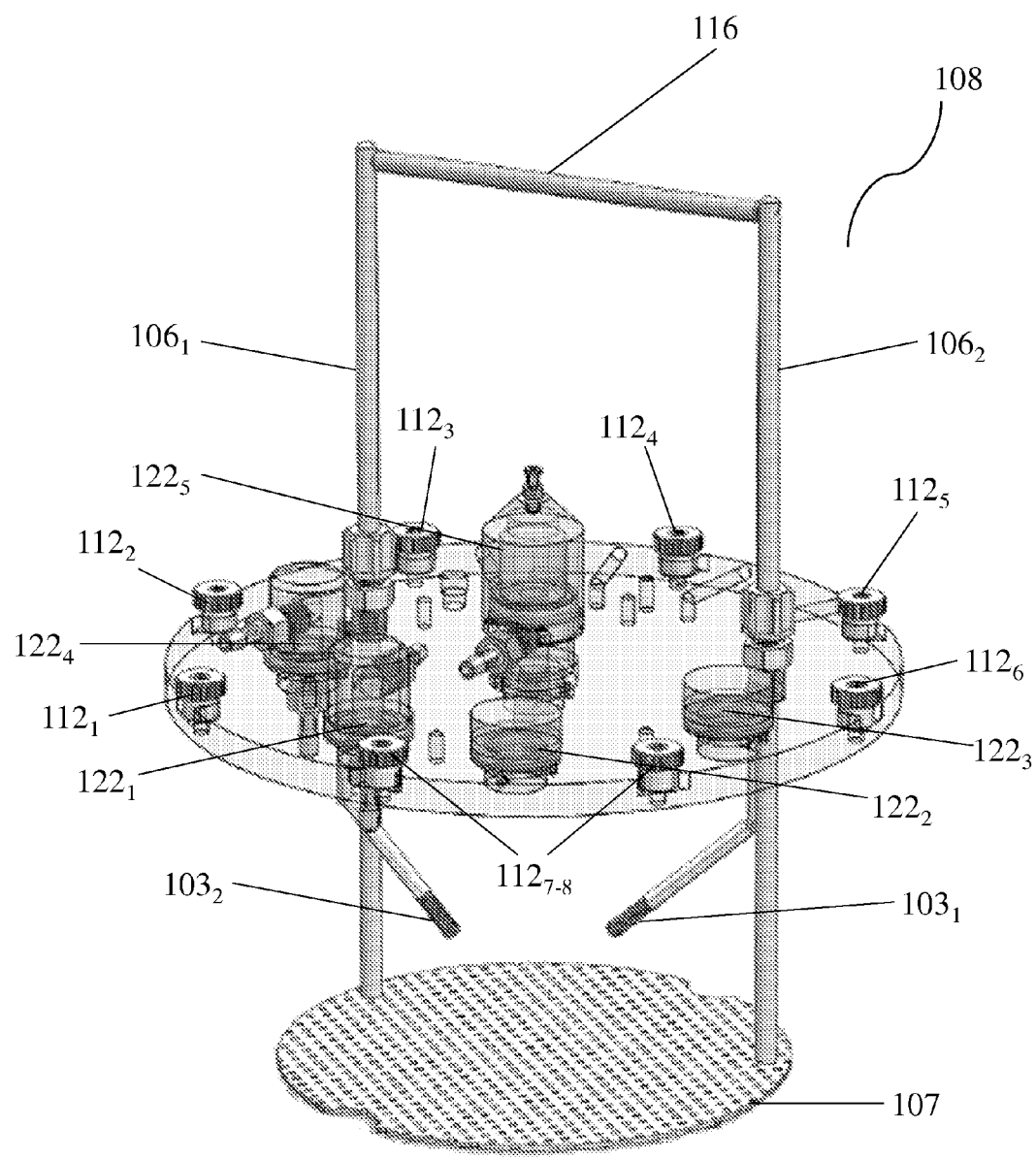
FIG. 3 depicts a cover assembly (108) of a bioreactor (100)

FIG. 3 depicts a cover assembly (108) for a bioreactor (100). The cover assembly (108) depicted has elongate members (1061-2) passing through the cover component (102) with fasteners (e.g. clamps, bolts) (1041-2) that may be used to releasably lock the elongate members (1061-2) in a position. Here again, an optional crossbar (116) may be used to join the elongate members (1061-2). Two elongate members (1061-2) are depicted orientated in substantial parallel to one another and perpendicularly to a support base (e.g., a platform or hammock like structure) (107). Elongate members (1061-2) may be connected to the support base (107) using any appropriate method. In the configuration depicted by FIG. 1, the support base (107) is variably positioned and fastened in place by clamps (1041-2). The cover component (102) contains a plurality of ports (1051-5); and holes (e.g. for fastening cover assembly to vessel) (112). Fluid conduits (e.g. cannula, drain etc.) (1031-2) are attached to and/or traverse ports providing access into the chamber.

While certain support bases depicted herein are attached to cover components, it should be appreciated that support bases can be movably attached to other aspects of a bioreactor including, for example, the inner wall of a bioreactor. For example, a support base may be connected to the inner wall of the bioreactor via guide rails or other components the permit the base to be maneuvered into or out from the bioreactor chamber. Motors or other motive devices may be configured with the support base to automatically, or upon a user's command, maneuver the base in a desired direction (e.g., up and down within the bioreactor).

Figure 4:
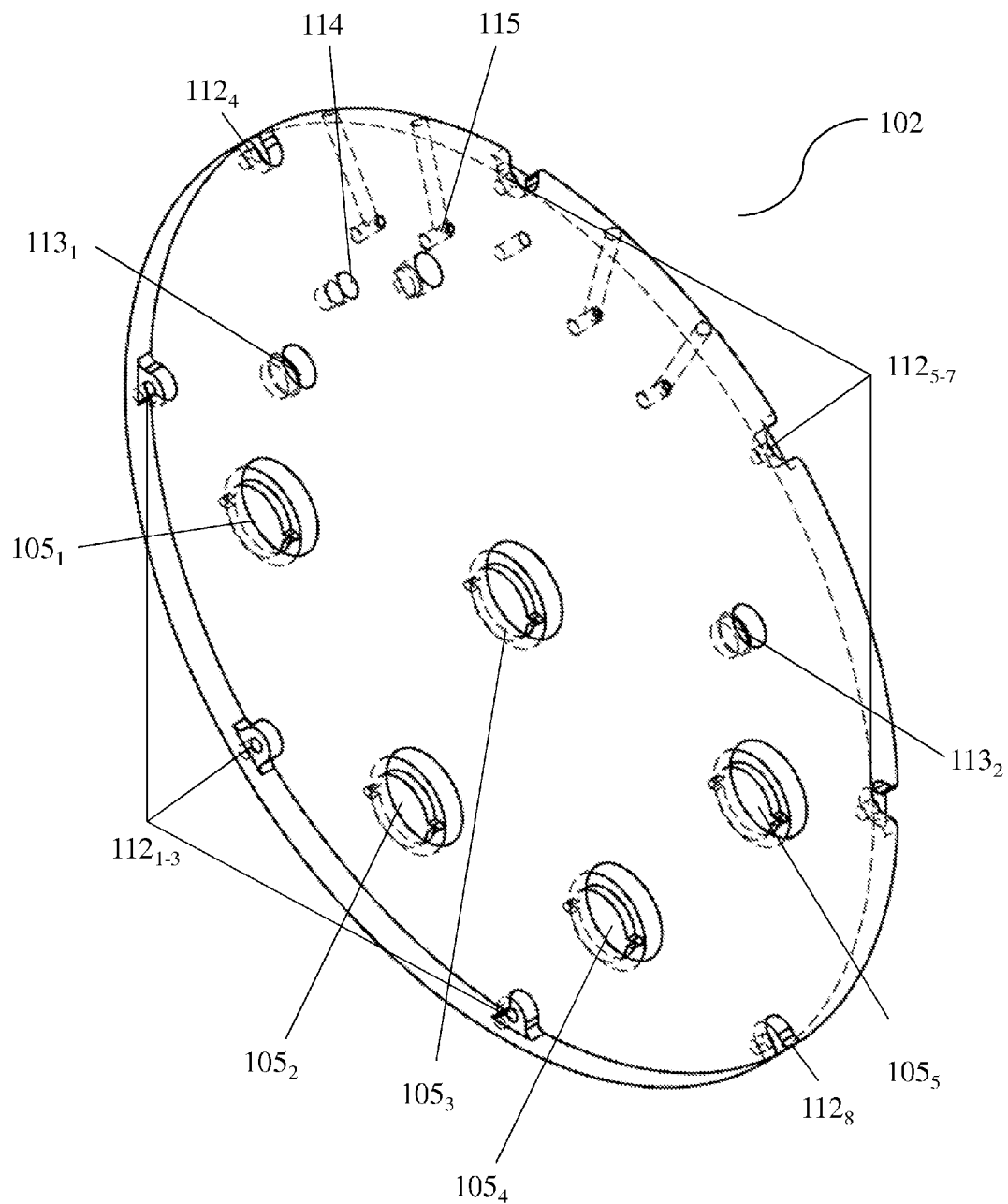
FIG. 4 depicts a cover component (102) of a bioreactor (100) with a plurality of different openings (e.g., ports)

In FIG. 4, a non-limiting example of a cover component (102) of a bioreactor (100) is depicted apart from the assembly. Holes (112) are shown on the periphery of the cover component. The holes may be used, for example, as bolt or screw holes for fastening the cover component to the vessel. However, in some embodiments of the cover component, holes are not provided for fastening the cover component to the vessel. In some embodiments, clamps are provided for fastening the cover component to the vessel. In some embodiments, an adhesive material is used to fasten the cover component to the vessel. In some embodiments, the cover is not fastened to the vessel. A plurality of ports (105) are shown in FIG. 4. A variety of components can be interconnected with the cover component through the ports. For example, one or more ports can be plugged. One or more ports may be fluidically connected with one or more fluid conduits. Such fluid conduits may be used for supplying or returning a perfusion fluid to or from the biological object. Holes with varying diameter (114, 115) are shown on the cover component and allow for further customization. Still, further configurations of holes, plugs and other aspects of the cover components may be provided.

Figure 5:
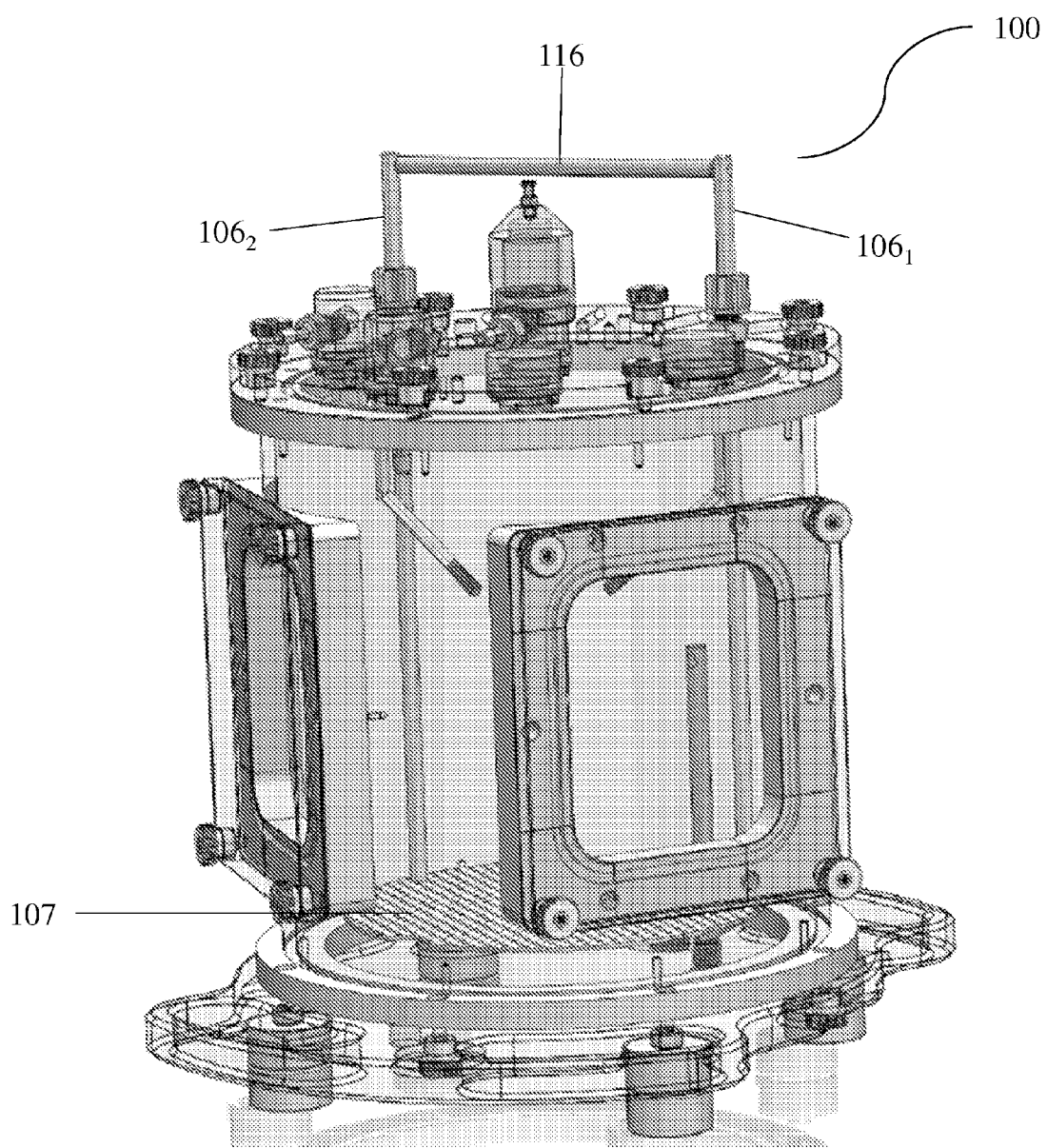
FIG. 5 depicts a bioreactor (100), in which the cover assembly (108) is joined with the vessel (109), and in which the support base (107) is depicted in a lowered position.

In FIG. 5 a non-limiting example of a bioreactor (100) is depicted as assembled. In this configuration, the cover assembly interface (101) of the vessel (109) is joined and fastened to the cover assembly. In some embodiments, holes (112) can be provided. In FIG. 5 a support base (107) is shown positioned at or near the bottom of the vessel (109). Elongate members (1061-2) connected to the support base (107) are correspondingly disposed in the vessel (109). The elongate members are here shown joined by an crossbar. However, in some embodiments, the elongate members are not joined by a crossbar.

Figure 6:
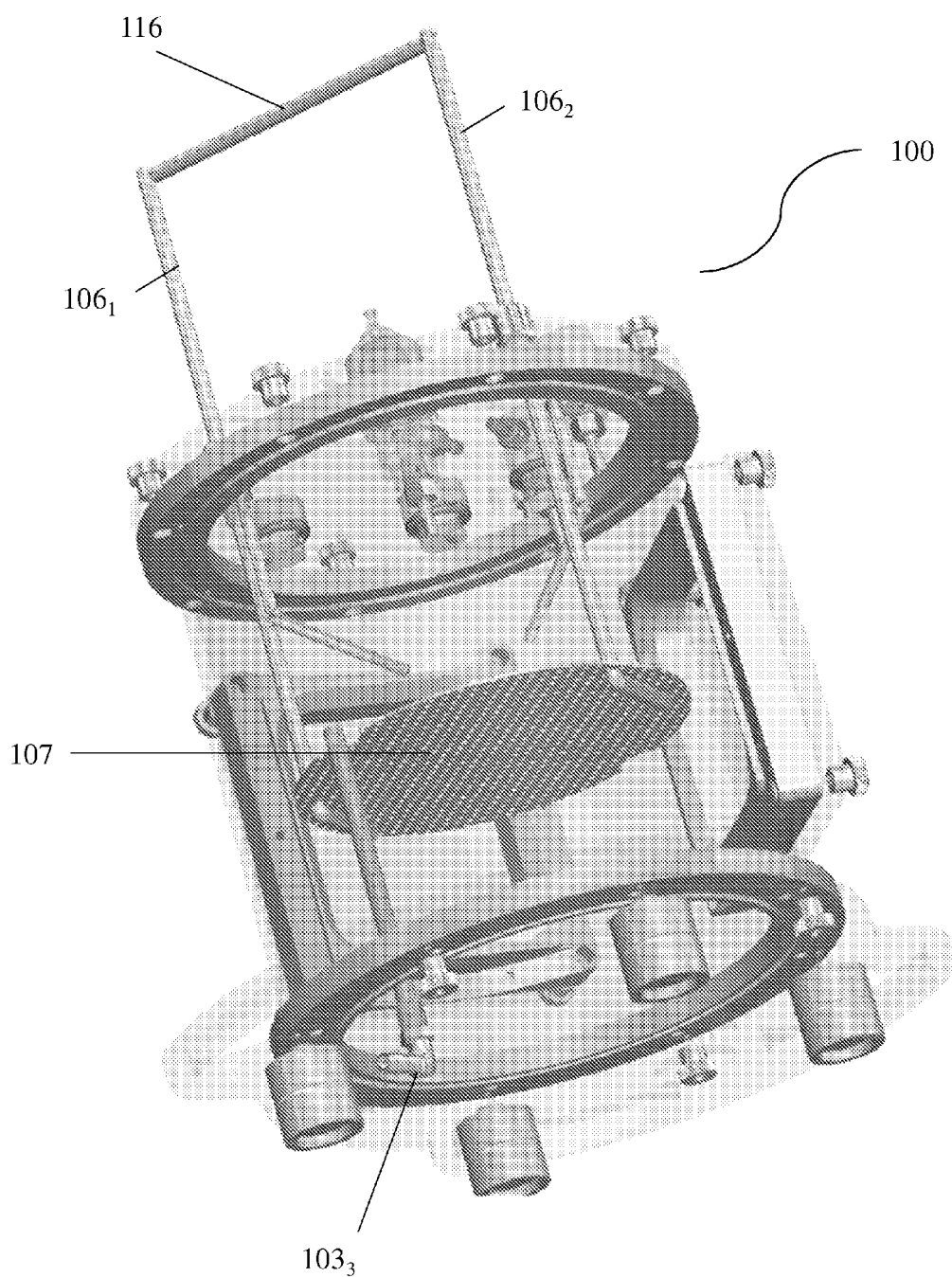
FIG. 6 depicts a bioreactor (100), in which the cover assembly (108) is joined with the vessel (109), and in which the support base (107) is depicted in a relatively raised position.

FIG. 6 depicts an assembled bioreactor (100), in which a cover assembly is joined with the vessel (109) and an interface (101). FIG. 6 depicts a configuration of the support base (107), in which the support base (107) is positioned within the vessel (109). In this example, the elongate members (1061-2) are joined by an optional crossbar. Elongate members (1061-2) attached to the support base (107) are correspondingly shown in a partially retracted position relative to the vessel (109). It should be appreciated that the support base (107) may be located at any suitable position relative to the cover component. In some embodiments, the support base is positioned in sufficient proximity to the cover component to maintain attachment of one or more fluid conduits of a biological component supported by the support base to one or more fluid conduits that supply or remove a perfusion medium to or from the biological component.

Figure 7:
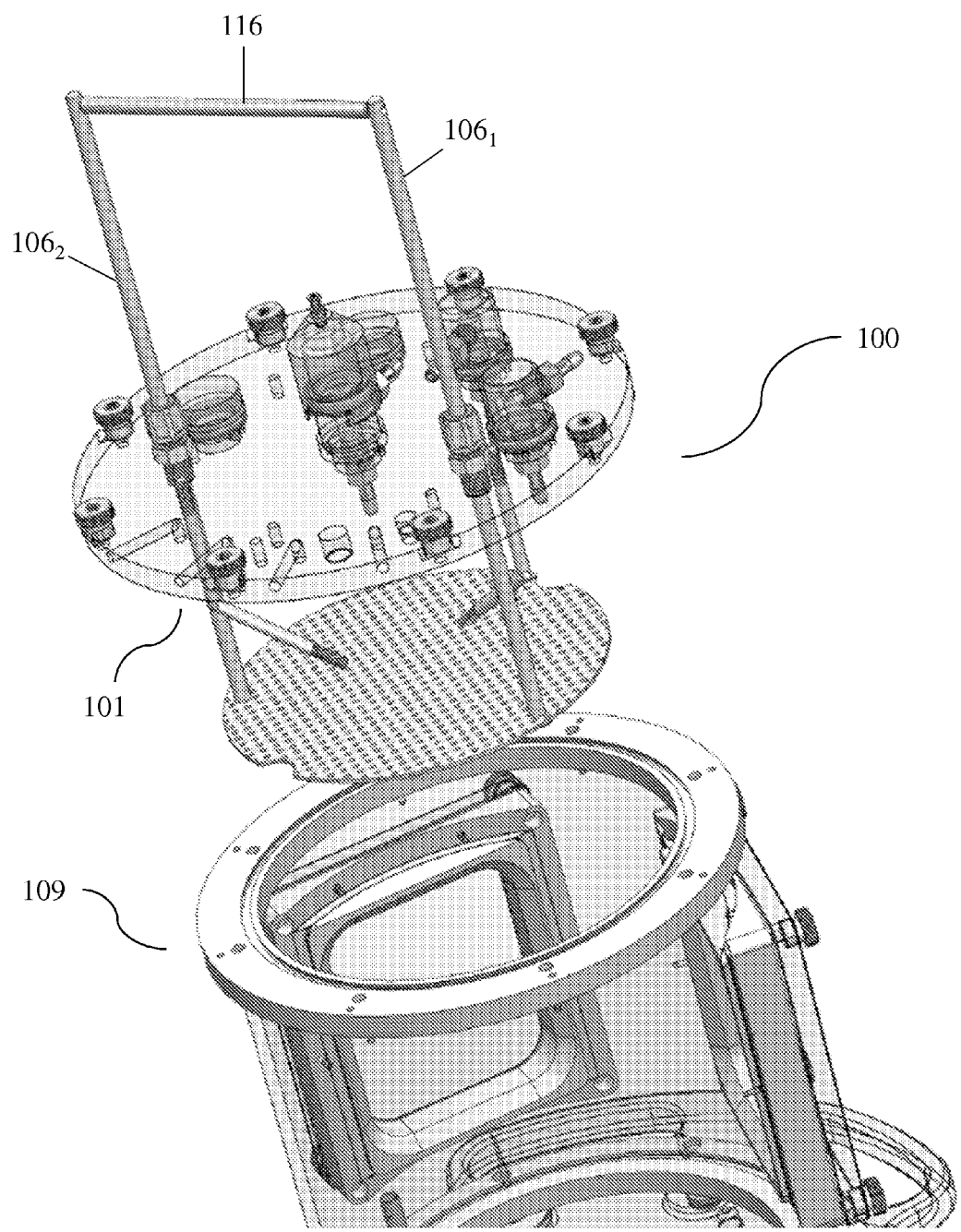
FIG. 7 depicts a bioreactor (100) comprising a cover assembly (108)) separate from a vessel (109)

FIG. 6 also depicts fluid conduits (e.g. cannula, drain) (1031-2) with angled flow paths, traversing the bottom of the vessel (109) and running up to the support base (107) perpendicularly, meeting the support base (107) near a mid-position in the vessel. Other suitable configurations of the fluid conduits may be provided. FIG. 7 depicts a bioreactor (100), where the cover assembly (101) arranged to be joined with the vessel (109).

Figure 8:
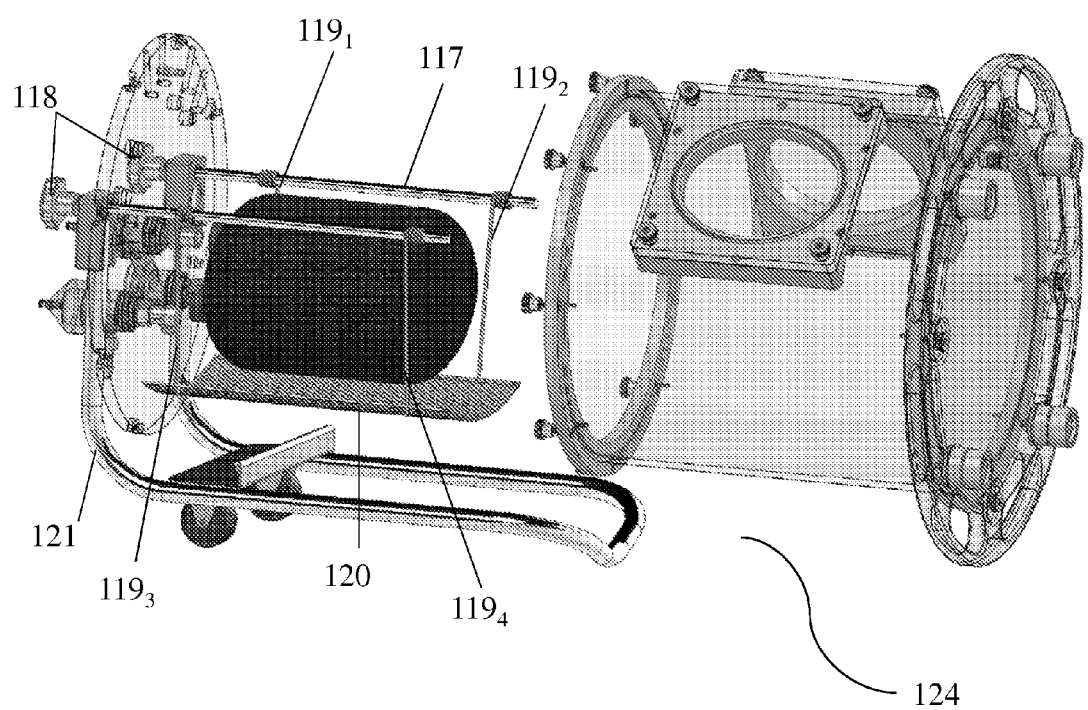
FIG. 8 depicts an alternative configuration of a bioreactor with a horizontally arranged support base (102) for supporting a biological object (e.g., an organ).

In FIG. 8 another configuration of a bioreactor (124) is depicted. In this configuration, a support base (120) is attached to straps (1191-4) (e.g., KEVLAR cord, metallic wire) which is attached to adjustable elongate members (118). In this embodiment, the elongate members are provided with knobs to facilitate rotational adjustment of the elongate members. The support base (120) may be attached to the straps (1191-4) using any suitable method (e.g., welding, bonding, bolting, tying). In the configuration depicted by FIG. 8, the straps (1191-4) extend vertically up from the support base (120) and wrap or coil around knobbed or adjustable (118) elongate members (118). In this configuration knobbed or adjustable (118) elongate members are able to rotate, allowing for coiling or uncoiling the straps (1191-4) connected to the support base (120), in this way the support base (120) may have its position adjusted relative to the elongate members. Other configurations for manipulating the relative position of the support base may be employed. FIG. 8 also depicts a roller assembly (121) configured to permit a user to move the support base (120) into the bioreactor vessel.

It should be understood that not all of the features shown in FIGS. 1-8 need be present in all embodiments of the disclosure and that the illustrated elements may be otherwise positioned or configured. Also, additional elements may be present in other embodiments, such as detectors and other elements described herein. Furthermore, not all of the features shown in FIGS. 1-8 need be present in the specific orientations shown. In general, as used herein, a component of a system disclosed herein that is "joined with" or "operatively joined with" one or more other components indicates that such components are directly connected or attached to each other, in direct physical contact with each other without being connected or attached to each other, or interconnected so as to cause or enable the components so associated to perform their intended functionality.

In some embodiments, especially in certain embodiments involving growing a tissue and/or organ in a bioreactor, the vessel containing the scaffold, tissue construct, organ, or other biological object is substantially closed, e.g., the vessel is substantially sealed from the environment outside of the vessel except, in certain embodiments, for one or more inlet, outlet and/or access ports that allow addition to and/or withdrawal of contents from the vessel. By maintaining a sterile seal, contamination caused by the component, such as from the external environment, may be reduced or avoided.

A vessel may have any suitable size for containing a liquid, biological object, or other entity. For example, the vessel may have a volume from about 0.1 L and about 0.5 L, about 0.1 L and about 1 L, about 1 L and about 5 L, and from about 1 L and about 10 L. Larger volumes are also possible (e.g., 10-20 L, 20-30 L, 30-40 L, 40-50 L, or larger). The volumes may depend on the particular use of the bioreactor (e.g., the size of the scaffold, the particular tissue or organ being grown, etc.).

In some embodiments, the vessel of a bioreactor may be attached to a system for maintaining and controlling growth conditions. Accordingly, the vessel may include one or more inlet and/or outlet ports for fluid connection with a system that may contain one or more reservoirs, pumps, controllers, etc., or any combination thereof. In some embodiments, a vessel may include one or more electrical and/or fiber-optic ports or conduits. In some embodiments, a vessel may be attached to a fixed support. However, in some embodiments, a vessel may be attached to a support via a mechanism that allows for motion in one or more directions.

The bioreactor and an associated control system may be constructed and arranged to provide one or more different culture conditions and/or operating parameters in one or more chambers. Such differentially provided/controlled parameters/conditions may include, but are not limited to culture media type, nutrient composition and concentration, dissolved oxygen concentration, dissolved carbon dioxide concentration, cell concentration, degree or existence of cell adherence to a substrate, temperature, media movement/fluid shear stress to which cells are exposed, pH, osmolality, etc. Such parameters can be measured over time to monitor viability and/or growth.

In bioreactors used for certain types of cell, tissue or organ cultivation, the cell, tissue or organ may require nutrients such as sugars, a nitrogen source (such as ammonia ($NH_3$) or amino acids), various salts, trace metals and oxygen to allow growth, division, and/or maintenance of such components. The amount of nutrients available to cells at any one time depends in part on the nutrient concentration in the liquid culture or in a solution perfusing one or more fluid conduits (e.g., vessels) of an organ (e.g., a substitute organ). It should be appreciated that an organ that is vascularized may be perfused using a suitable solution that may mimic one or more features of blood (e.g., provides oxygen and nutrients and removes carbon dioxide and waste products). In some embodiments, the perfusate may be artificial blood. In some embodiments, the perfusate may be a blood product (e.g., blood or blood processed to retain certain components that are useful for oxygen, nutrient, waste product, and other transport). It should be appreciated that any suitable perfusate may be used depending on the functional requirements (e.g., having oxygen carrying properties, energy carrying properties, waste carrying properties, other properties, or any combination thereof). Sugars, nitrogen sources, salts, and trace metals may be soluble in a liquid and, therefore, may be readily available by replenishing the cells with fresh liquid media. In some cases, liquids can be introduced into one or more chambers of a bioreactor via one or more inlets described herein. The one or more inlets may be in fluid communication with one or more adjustable pumps, which are connected to sources of fluid containing appropriate combination of nutrients. In embodiments in which the percentage of different components changes depending on the stage of growth, the different components can be added together in real-time to form a media composition suitable for that growth stage. This can be done through a feedback system where one or more sensors measures the composition of the liquid(s) in the chamber(s), sends the values to a computer, which then determines what composition of fresh media is needed. After the media is formed, it can be delivered continuously or periodically to the appropriate chamber at a suitable flow rate and volume. Each chamber can include such a control system for maintaining a specified growth condition in the chamber.

It should be appreciated that one or more inlets and/or one or more outlets may be connected to a fluid containing zone (e.g., at the bottom of a chamber when in use); and/or to a gas containing zone (e.g., at the top of a chamber, above the fluid at the bottom of the chamber, when in use), and/or to afferent and/or efferent vessels of the growing organ. In some embodiments, a reactor may include any combination of two or three of these configurations. Accordingly, the external and/or internal environment of the organ may be separately and independently monitored and/or regulated through sensors, pumps, controller, and other components that may be independently connected to each of these three or more regions (external fluid, external gas, internal fluid—for example via a circulatory system, internal gas—for example via respiratory pathways, or others). Note that in some embodiments, a liquid solution may be used to perfuse airways during development (e.g., of a lung). In some embodiments, this may be replaced with a gas (and the relative pressures may be changed) at an appropriate time during development.

Like the other nutrients, even and uniform distribution of oxygen throughout the chamber(s) of a bioreactor may be essential to provide uniform cell, tissue, or organ growth. Poor distribution of oxygen can create pockets of cells deprived of oxygen, leading to slower growth, alteration of the cell metabolism or even cell death. In addition, the presence of salts plus the elevated temperature necessary to grow certain cells, tissues and organs may further reduce dissolved oxygen concentration. Since oxygen may be relatively poorly soluble or "dissolved" in water, it can be delivered to the cells by a supply of gas.

In other embodiments, oxygen and/or other gases can be introduced into a bioreactor to compensate for depletion of oxygen or other gases. As described herein, a bioreactor may include a port that is dimensioned for connection to different sources of gas, which may be independently controlled. The type of gas, number of ports, and types and configurations of ports of a bioreactor may depend, in part, on the particular processes to be carried out and cells/tissues/organs to be grown. In one embodiment, a bioreactor includes sources for different types of gases such as a dissolved oxygen control gas for controlling the amount of dissolved oxygen in the culture fluid and a pH control gas for controlling the pH of the culture fluid. For example, carbon dioxide may be used to increase solution pH and ammonia may be used to decrease solution pH. In one embodiment, a pH control gas may include a combination of carbon dioxide, ammonia, or other gases to control (e.g., increase or decrease) pH. Each type of gas may be introduced into and/or removed from the culture using different ports that can be independently operated and controlled.

Gases may be introduced continuously, periodically, or in some cases, in response to certain events, e.g., within a bioreactor system and/or within the vessel. For example, gas inlets may be connected to one or more sensors and a control system which is able to monitor the amount of gas introduced, pH, and/or the amount or concentration of a substance in the vessel, and respond by initiating, reducing, or increasing the degree of gas introduction of one or more composition(s) of gases.

In some embodiments, the vessel or chamber can be operatively associated with a variety of components as part of an overall bioreactor system. Accordingly, the vessel may include several fittings to facilitate connection to functional component such as filters, sensors, pumps and mixers, as well as connections to lines for providing reagents such as liquid media and gases.

In some embodiments, for certain organs, particularly relatively large organs (e.g., lung, heart, intestine, liver etc.), an device is provided that can hold and support the organs external to the bioreactor so that cannulation, suturing and/or all or any manipulations that may be desirable for purposes of preparing an organ for growth in the bioreactor can be performed. In some embodiments, the device can handle natural organs which will be surgically manipulated, or natural organs to be decellurized and/or recellurized or synthetic scaffolds. The external device may be configured such that the tissue or organ can be supported by the device while configured with lines, cannula or other components. In some embodiments, the external support device is configured such that its position is readily maneuverable or manipulatable by one or a few people and can be transferred or repositioned into the bioreactor chamber or used to transfer a tissue or organ onto a support base of a bioreactor.

Uses

In some embodiments, the bioreactor device can be used to decellularize natural scaffolds, recellularize scaffolds (natural or synthetic), culture and grow tissue and organ, and/or condition synthetic material (e.g., to coat it with a biologically compatible material), etc. However, it should be appreciated that any of the bioreactors described herein may be used to grow an organ (e.g., a substitute organ) for research and/or for clinical transplantation. As used herein an organ (e.g., a substitute organ) may be a complete organ or a partial organ that has at least one or more physiological functions of an organ. For example, a partial kidney may produce erythropoietin (EPO) but not filter the blood. Accordingly, in some embodiments, a partial organ may have one or more secretory functions of an organ (e.g., it produces and/or secretes one or more compounds, for example a hormone, that a natural organ produces and/or secretes). However, a partial organ may have one or more other properties of an organ as the disclosure is not limited in this respect. For example, a partial organ may perform one or more detoxification properties of a liver. In some embodiments, an organ (e.g., a substitute organ) may be grown on a scaffold (e.g., a natural or synthetic scaffold). In some embodiments, an organ (e.g., a substitute organ) may be based on a decellularized scaffold of a first organ that is recellularized with cells of the same organ type to reconstitute similar organ functions. In some embodiments, an organ (e.g., a substitute organ) may be based on a decellularized scaffold of a first organ that is recellularized with cells from a different second organ. For example, a first organ (e.g., kidney) may be decellularized and the resulting scaffold may be recellularized with cells that have one or more properties (e.g., secretory properties) of a second organ (e.g., liver). In some embodiments, a kidney may be a useful first organ to use to produce a scaffold since a subject has two kidneys and one of them may be removed to produce a scaffold for an organ (e.g., a substitute organ) in the same subject. In some embodiments, one or more growth parameters may be similar to physiological conditions (e.g., temperature around 37° C., physiological pH, etc.)

In some embodiments a biological object comprises a scaffold upon which cells can be seeded. In some embodiments, the scaffold is a matrix. In some embodiments, the scaffold comprises an axis. In some embodiments, the bioreactor comprises a support structure, e.g., connected to the cover component that is capable of rotating around one or more axes. A bioreactor may be provided without a scaffold and include one or more support structures attached (e.g., releasably attached) to the cover component to which a scaffold may be attached. A bioreactor may include one or more support structures attached to the cover component to support the weight of a growing organ. It should be appreciated that a structure to which a scaffold is attached also may support the weight of a growing organ. However, one or more scaffold and organ support structures may be different as described herein. In some embodiments, an organ (e.g., a substitute organ) may be grown without using a scaffold, but the weight of the organ could be supported by one or more structures within a bioreactor. It should be appreciated that one or a plurality of attachment points for the scaffold (e.g., 2-5, 5-10, or more) may be provided on a cover assembly, support structure, support base or other component.

However, as described in more detail herein, an organ (e.g., a substitute organ) can be produced without a scaffold. For example, in some embodiments, an organ (e.g., a substitute organ) can be based on a micro-channel containing device having tissues that are grown to produce particular chemicals or to perform particular detoxification steps that can mimic one or more functions of a natural organ. It should be appreciated that these can be single or multilayer devices with no scaffold that act like an organ when transplanted into a host.

As described herein, in some embodiments, aspects of the disclosure relate to growing cells to form cellular tissues, organ-like structures, and/or complete organs within the bioreactor. In some embodiments, the tissue or organ-like structures are grown to form cavities surrounded by a cellular layer. In some embodiments, the tissue or organ-like structures are grown in the form of tubular structures. In some embodiments, the tubular structures may be airway structures (e.g., trachea, bronchi, bronchioles, or other airway passages), blood vessels (e.g., arteries, veins, vessels, capillaries), tubular portions of other organs (e.g., kidney, esophagus, gut, stomach, intestine, colon, large intestine, small intestine, ducts, pancreatic duct, bile duct, gall bladder, bladder, urethra, urogenital structures, oronasal structures). It should be appreciated that tubular structures of the disclosure do not necessarily form perfect geometrical tubes. The shape of a tissue may be varied. In some embodiments, body cavities surrounded by a cellular layer may be created. For example, structures that mimic alveoli, heart cavities, kidney cavities, other organ or body cavities (e.g., ones that contain more or less actual tubular regions) may be grown or assembled according to aspects of the disclosure. It should be appreciated that the size of a tubular structure may be determined by the size of the support on which it is grown. Accordingly, the diameter and/or length may be determined by specifying the diameter and/or length of the acellular support (e.g., support matrix). Accordingly, a tubular tissue structure grown on the support may only represent a partial length of a tubular structure in a subject. For example, a length of airway or blood vessel grown in a bioreactor may be a portion of the length of the corresponding airway or blood vessel in a subject (e.g., in a human or animal).

Methods and devices described herein may be useful for implementing substitute tissue and organ growth in a production context as opposed to a small-scale research context. In some embodiments, aspects of the disclosure address transport, storage, tracking, sterility, functional screening, and other challenges associated with large scale organ (e.g., a substitute organ) or tissue production.

In some embodiments, the tissues or organs being grown and/or analyzed are in vivo. In other embodiments the tissues or organs being grown and/or analyzed are ex vivo. In certain embodiments, the organ is an organ (e.g., a substitute organ). As used herein, an organ (e.g., a substitute organ) can be an entire or partial organ, or tissue, or material that is engineered to perform one or more functions of an organ (but not necessarily the entire function of an organ). In some embodiments, an organ (e.g., a substitute organ) may be produced to replace or supplement one or more functions of any organ or tissue, including but not limited to an adrenal gland, appendix, artery, brain tissue, bladder, bone, bronchus, cartilage, cornea, diaphragm, esophagus, eye, or more endocrine glands, fallopian tube, gallbladder, heart, hypothalamus, intestine, kidney, larynx, ligament, liver, mammary gland muscle, nerve, pancreas, pharynx, pineal body, lymph node, lung, spleen, stomach, ovary, parathyroid gland, pituitary gland, prostate, testicle, thymus, trachea, ureter, uterus, urethra, urinary bladder, vein, other organ, or any combination thereof.

Methods and devices of the disclosure may be used to grow, store, and/or transport any suitable organ (e.g., a substitute organ) or tissue regardless of its source. In some embodiments, an organ (e.g., a substitute organ) or tissue may be initiated by populating a scaffold with appropriate cells. In certain embodiments, an organ (e.g., a substitute organ) or tissue may result from the growth and development of an initial set of cells without the aid of an external scaffold. In certain embodiments, an organ (e.g., a substitute organ) or tissue may be provided by starting with an existing organ or tissue or portion thereof (e.g., from a donor) and incubating it in a reactor to promote further growth and/or development. However, it should be appreciated that certain embodiments described herein also may be used to promote the functional health and viability of a fully grown organ that was obtained from a donor.

In some embodiments, an organ (e.g., a substitute organ) may contain one or more cell types that are being regenerated on a scaffold to form the organ substitute. The scaffold may contain biological and/or artificial material (e.g., biological and/or artificial polymers). In some embodiments, the scaffold may consist entirely of biological material (e.g., one or more biological polymers). In some embodiments, the scaffold may consist entirely of artificial material (e.g., one or more synthetic polymers). In some embodiments, a scaffold may include a mixture of one or more biological materials and/or one or more artificial materials. In some embodiments, the materials are shaped (e.g., on a template, in a mold, or using any other suitable shaping technique, or any combination thereof) to have a suitable conformation (e.g., a three-dimensional conformation) and size (e.g., volume of cells, diameter and/or length of blood vessels, airways, and/or other ducts, etc.). It should be appreciated that the conformation and/or size of an organ (e.g., a substitute organ) may depend on the intended application (e.g., whether the organ (e.g., a substitute organ) is intended to replace an existing organ that will be removed or whether it is intended to supplement one or more functions of a deteriorating or failing or partially failing organ that remains in the patient).

Scaffolds:

As noted herein, cells, tissues and/or organs may be grown on a scaffold that is positioned within a chamber of a bioreactor as described herein. In growing tissues and/or organs of the body, different types of cells can be arranged proximate a scaffold in sophisticated organizations or architectures that are responsible for the complex functions of the tissue or organ. Thus, architectures having dimensions and arrangements closely related to the natural conditions of the tissue or organ can be formed. The design of the scaffold and the arrangement of cells within the scaffold can allow functional interplay between relevant cells, e.g., between cells cultured on the scaffold and those of the host environment. These factors may also enable appropriate host responses, e.g., lack of blood clotting, resistance to bacterial colonization, and normal healing, when implanted into a mammalian system.

A variety of different scaffolds can be used for seeding, growing, supporting, or maintaining cells, tissues, and organs as described herein. A scaffold can have any suitable shape and may depend on the particular tissue and/or organ to be grown. For example, the scaffold may be substantially tubular, substantially cylindrical, substantially spherical, substantially planar, substantially ellipsoidal, disk-like, sheet-like, or irregularly shaped. The scaffold can also have branching structures, e.g., to mimic arteries, veins, or other vessels. In certain embodiments, at least a portion of the scaffold is hollow.

In some embodiments, nanofiber or electrospun scaffolds are used for seeding, growing, supporting, or maintaining cells, tissues, and organs as described herein.

Scaffolds may be formed of natural and/or artificial materials. Materials used to form scaffolds may be biocompatible, and can include synthetic or natural polymers, inorganic materials (e.g., ceramics, glass, hydroxyapatite and calcium carbonate), composites of inorganic materials with polymers, and gels. All or a portion of a scaffold may be formed in a material that is non-biodegradable or biodegradable (e.g., via hydrolysis or enzymatic cleavage). In some embodiments, biodegradable polyesters such as polylactide, polyglycolide, and other alpha-hydroxy acids can be used to form scaffold. By varying the monomer ratios, for example, in lactide/glycolide copolymers, physical properties and degradation times of the scaffold can be varied. For instance, poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded. A portion of a scaffold that is biodegradable may, in some embodiments, degrade during the growth of cells, tissues and/or organs in the bioreactor. In other embodiments, degradation may take place after implanting the tissue or organ in a recipient.

A scaffold may, in some cases, be formed of a biological material, such as a tissue construct. In certain embodiments, at least a portion of the tissue construct is acellular. In certain embodiments, the at least partially acellular tissue construct comprises tissue that has been decellularized. In the description herein concerning the use of appropriate materials to fabricate scaffolds, those of ordinary skill in the art can select materials, techniques, etc. based upon general knowledge of the art and available reference materials concerning certain techniques for fabrication, in combination with the description herein. In some cases, combinations of natural and artificial materials can be used.

Scaffolds may be porous or substantially nonporous. In some instances, the wall of a scaffold includes pores having a cross-sectional dimension of less than or equal to 1 mm, less than or equal to 100 microns, less than or equal to 50 microns, less than or equal to 40 microns, less than or equal to 30 microns, less than or equal to 10 microns, less than or equal to 5 microns, less than or equal to 1 micron, or less than or equal to 100 nm. A variety of techniques can be used for introducing porosity into a scaffold. For instance, porosity can be induced by methods such as solution casting, emulsion casting, polymer blending, and phase transition induced porosity.

Scaffolds can have various dimensions which may depend on the particular use of the scaffold. A scaffold may have an average thickness of, for example, between 1 micron and 1 mm, between 10 microns and 0.5 mm, between 1 mm and 5 cm, between 1 mm and 1 cm, between 1 cm and 10 cm, or between 1 cm and 5 cm. Other thicknesses are also possible. The largest cross-sectional dimension of the scaffold can also vary from, for example, between 1 micron and 1 mm, between 10 microns and 0.5 mm, between 1 mm and 5 cm, between 1 mm and 1 cm, between 1 cm and 10 cm, between 1 cm and 5 cm, between 1 cm and 20 cm, or between 10 cm and 20 cm. A length of the scaffold can also vary from, for example, between 1 mm and 5 cm, between 1 cm and 10 cm, between 1 cm and 5 cm, between 1 cm and 20 cm, or between 10 cm and 20 cm. Other lengths are also possible. A scaffold may also have an aspect ratio (length to average cross-sectional dimension) of at least 2:1, 3:1, 5:1, or 10:1 or more. It also should be appreciated that the size and thickness of a scaffold may vary over its shape (e.g., length, width, etc.). In some embodiments, a scaffold may include a series of zones of different thicknesses (e.g., forming a pattern of different thicknesses that may provide different structural properties).

Optionally, surface properties of a scaffold can be modified by various techniques. For example, in some cases, surfaces of a scaffold can be modified by coating and/or printing an additive proximate the structure. Surfaces may be modified with additives such as proteins and/or other suitable surface-modifying substances. For example, collagen, fibronectin, an RGD peptide, and/or other extracellular matrix (ECM) proteins or growth factors can be coated onto the scaffold, e.g., to elicit an appropriate biological response from cells, including cell attachment, migration, proliferation, differentiation, and gene expression. Cells can then be seeded onto surfaces of the scaffold. In one embodiment, cell adhesion proteins can be incorporated into certain portions of a scaffold to facilitate ingrowth of blood vessels. In another embodiment, growth factors can be incorporated into the scaffold to induce optimal cell growth conditions that trigger healthy tissue formation within certain regions of the scaffold. In other cases, additives can be incorporated into the material used to form the scaffold (e.g., embedded in the scaffold during fabrication).

In some cases, it may be desirable to modify all or portions of a scaffold with a material that inhibits cell adhesion, such as a surfactant (e.g., polyethylene glycol and polypropylene oxide-polyethylene oxide block copolymers). For instance, areas of a scaffold where it is not desirable for cellular growth can be coated with such materials, e.g., to prevent excessive soft connective tissue ingrowth into the structure from the surrounding tissue. In some cases, modification of surface properties of the scaffold can be used to position cells at specific sites on or within the scaffold. In some embodiments, a combination of cell-adhering and cell-inhibiting substances can be incorporated into various portions of a scaffold to simultaneously facilitate and inhibit cell growth, respectively.

In some embodiments, a scaffold can be coated with a porous material (e.g., a polymer such as a gel), e.g., prior to or during the seeding of cells. A porous polymer coating a scaffold can be used for a variety of purposes. For example, a porous polymer may be used to form pores on a scaffold that is otherwise non-porous. The porous polymer may allow, for example, sustained release of an active agent from the scaffold, e.g., to facilitate cell growth and/or cell adhesion as a function of time.

As described herein, cells may be seeded on various portions of a scaffold either before or after the scaffold is positioned in a bioreactor. In certain embodiments, cells may be seeded on at least one surface or region of a scaffold (e.g., a decellularized tissue construct) such that the cells are contained within at least one structural region of a bioreactor defined by a scaffold. In certain embodiments, cells are seeded on two or more regions or surfaces of a scaffold. In certain such embodiments, the cells on the first region or surface are of the same type as the cells on the second region or surface and in other embodiments they are of different types. In certain embodiments, at least one of the cell types on at least one of the first and second region or surface is of a type normally associated with the type of tissue comprising a decellularized tissue construct in vivo.

It should be appreciated that the cell types used to seed a bioreactor of the disclosure may be selected based on the type of tissue or organ structure that is being grown. In some embodiments, the cells may be epithelial, endothelial, mesothelial, connective tissue cells, fibroblasts, etc., or any combination thereof. In some embodiments, cells may be stem cells, or pluripotent or totipotent cells. In some embodiments, different cells may be used to seed different portions of a scaffold. In some embodiments, one or more growth factors may be provided to promote appropriate growth and/or differentiation of the cells.

Decellularized Organ/Tissue:

In some embodiments a scaffold may be derived from an existing tissue or organ. For example, a tissue or organ may be decellularized to reveal a scaffold that can then be recellularized (e.g., with one or more patient-specific or patient-compatible cells lines) to form an organ substitute that can be implanted into a patient. A decellularized scaffold may be based on any suitable organ or tissue from any suitable organism. After decellularization, the remaining scaffold provides a structure that can be used to form an organ that has the same overall size and architecture as the original organ. However, it should be appreciated that a variety of different functions may be provided depending on the cells that are used for recellularization. Accordingly, in some embodiments, an organ scaffold may be recellularized with the same cells types that were present in the original organ to restore the same set of functions as the original organ. However, in other embodiments, only a subset of the cells may be used to generate an organ (e.g., a substitute organ) that only has a subset of the original organ functions. In yet further embodiments, alternative or additional cells types may be used for recellularization, thereby providing an organ substitute that has alternative or additional functional properties.

Accordingly, the original architecture may be used as a support for a general organ function by, for example, providing suitable vascularization and structural support for the cells that are used to repopulate the organ or tissue structure. In some embodiments, an organ or tissue used for decellularization may be derived from the same species (e.g., from another human, for example a human cadaver). However, in some embodiments, an organ or tissue used for decellularization may be derived from a different species. It should be appreciated that the selection of the species may be based on one or more factors including: the size of the structure that is required, the degree of vascularization that is required, the likelihood of undesirable immune response (e.g., rejection) against the scaffold (even though a decellularized scaffold is less immunogenic due to the removal of cellular antigens, there is a potential for an immune response due either to the presence of a small residue of cellular antigens, and/or an immune response against the scaffold material itself). In some embodiments, a scaffold may be obtained from any suitable mammal (including a pig, goat, sheep, etc.).

It should be appreciated that a decellularized organ or tissue may be used directly as a scaffold for recellularization. However, in some embodiments, the decellularized material may be further manipulated to alter its shape and/or size, and/or to add features (e.g., structures such as tabs, additional material, shapes that are easier to suture, etc.) i) to help support (e.g., physically support) the organ (e.g., a substitute organ) during recellularization and growth in a bioreactor, ii) to assist with removing the organ (e.g., a substitute organ) from the bioreactor, iii) to assist with implanting the organ (e.g., a substitute organ) into the recipient, iv) to assist with providing support for and/or monitoring the organ (e.g., a substitute organ) after implantation into a recipient. For example, in some embodiments, a scaffold may be shaped or modified to include extensions (e.g., tubular extensions) for support growth of longer vessels or other tubular structures, longer or larger sections of connective tissue, or other additional tissue relative to that found on a natural organ. For example, shapes for vessels or other structures that are about 10%, about 25%, about 50%, about 75%, about 100%, or about 2, 3, 4, or 5 fold longer (or more, or any intermediate value or any range between any of these values) than a typical length of the vessel or structure that protrudes from the natural organ (e.g., than was present on the scaffold resulting from organ decellularization).

In some embodiments, adipose tissue may be decellularized to provide a scaffold that can be recellularized with one or more cell lines to generate an organ (e.g., a substitute organ) that has at least one property of a different organ or tissue (e.g., a liver, kidney, heart, lung, pancreatic, or other organ function).

In some embodiments, an organ or tissue may be decellularized in an expanded position. Rather than simply perfusing an organ being decellularized, a positive or negative pressure (static or cycling) may be applied to the tissue or organ being decellularized. For example, for a lung, a negative or positive pressure may be applied to the organ so that the scaffold can expand and thus expose the scaffold to decellularizing material (e.g., detergent) in a stretched out position. For a solid organ like a kidney, a positive or negative pressure could be created to expand the organ and its tissue to expose the organ to decellularizing material (e.g., a detergent solution, for example containing SDS; an enzymatic solution, for example containing an RNase, a DNase; with or without TritonX-100; with or without EDTA or sodium-deoxycholate; or any other suitable material) in the expanded state.

In some embodiments, the status of an organ (e.g., an artificial organ) may be evaluated in an expanded or pressurized position. This may involve a pulsatile or continuous pressure (e.g., positive or negative pressure, or a cycle of one to the other).

According to aspects of the disclosure, if decellularization is performed using just a perfusing flow of material, the scaffold tissue may not be sufficiently expanded and exposed to the material (e.g., detergents, enzymatic preparations, or other solutions as described herein). By expanding (e.g., using a fluid or gas to pressurize internal cavities of an organ or by stretching (e.g., pulling, twisting, etc., or any combination thereof) two or more portions of the organ or tissue relative to each other, a more uniform exposure to decellularizing material may be obtained. This is advantageous for at least two reasons: i) certain tissue regions that are generally not very accessible (e.g., due to folds or other structures) can be exposed and more completely decellularized by stretching, and/or ii) over-exposure of regions that are readily accessible is reduced or avoided, because the entire organ or tissue does not need to be exposed to decellularizing material for as much time if the accessibility of "hidden" regions is increased by expanding or stretching.

It should be appreciated that the forces used to expand or stretch an organ during decellularization may be natural physiological forces or pressure (e.g., blood pressure, air pressure in lungs, forces exerted by a muscle such as a heart or other muscle, etc., or any combination thereof). It should be appreciated that natural pressure and forces are higher than those exerted by a simple perfusion with or bathing of an organ in decellularizing material. In some embodiments, a pressure or force that is either higher than a natural force or pressure may be used (e.g., about 10%, about 25%, about 50%, about 75%, about 100%, or 2, 3, 4, 5, fold higher, or higher than any of these values, or any intermediate level or range between these values) may be used provided it does not destroy the scaffold of the tissue or organ being decellularized. In some embodiments, a force or pressure that is higher than a low pressure perfusion or a bathing solution may be used even if it is slightly lower than a natural force or pressure (e.g., about 10%, about 25%, about 50%, about 75%, about 100%, or 2, 3, 4, 5, fold lower, or lower than any of these values, or any intermediate level or range between these values).

It also should be appreciated that other decellularization techniques (e.g., using mechanical or physical forces or energy, with or without other chemical compositions) may be used in combination with the expanded tissue as described herein.

Sterility:

In some embodiments, aspects of the disclosure relate to providing a sterile environment for the growth of an organ (e.g., a substitute organ). Systems and procedures that enhance sterility provide a significant advantage in a high volume system.

In some embodiments, methods and devices are provided to demonstrate that an organ is sterile by showing that the organ has been grown in compliance with sterile techniques. However, in some embodiments, methods and devices include a test or assay that allows for positive confirmation that an organ (e.g., a substitute organ) is in fact sterile. In some embodiments, the presence of one or more contaminating cells or microorganisms (e.g., bacteria, viruses, fungi, yeast, other contaminating unicellular organisms) and/or contaminating multicellular organisms may be tested for directly. In some embodiments, a test may assay for the presence of one or more contaminating molecules indicative of the presence of a contaminating organism (e.g., protein, DNA, RNA, and/or other metabolic traces of a contaminating cell or organism).

In some embodiments, aspects of the disclosure relate to procedures for ensuring sterility. In some embodiments, a device may include one or more ports and/or tools that allow material to be added to and/or removed from a reactor chamber under sterile conditions. In some embodiments, a sterile closed system is provided that contains all material required for organ growth, testing, etc., or any combination thereof. In some embodiments, a closed system contains all the material required for initial growth of an organ (e.g., a substitute organ) (e.g., prior to challenging the organ (e.g., a substitute organ) to determine that it has one or more desired functional and/or structural properties). In some embodiments, a multistage system may be sterilized and include different zones attached to different sensors, inputs, outputs, reservoirs, manipulators, stimulators, etc., each of which can be disconnected or removed while maintaining sterility.

It should be appreciated that aspects of the disclosure relate to kits that contain prepackaged material (concentrate, etc., that may be sterilized) that can be added to a bioreactor; sterile/sterilizable connectors for sampling and/or adding material; filters for continuous filtering under sterile conditions; other components required for sterile growth or testing, or any combination of two or more thereof.

In some embodiments, a device may include one or more features for protecting and/or confirming the sterility of the contents. In some embodiments, a mechanism may be provided for confirming that the reactor chamber has not been opened. In some embodiments, the mechanism is a physical mechanism that prevents the chamber from being opened until it reaches the surgical site (e.g., using a lock that is controlled by a key or by electronic information that is provided separately). In some embodiments, the mechanism provides a signal if the chamber has been opened. The signal could be an electronic or physical signal that indicates that a chamber has been opened (e.g., an alarm, trip, interlock or other suitable component may be used to generate a visible or audible signal, for example, a light, a flag, a beep, etc., or any combination thereof) or a signal that can be recorded (e.g., an entry in a database, a code, or other information) and identified at any suitable time (e.g., prior to surgery). In some embodiments, a "seal" is affixed to the chamber in such a way that it is broken when the chamber is opened thereby providing a signal that the chamber has been opened. In some embodiments, the chamber includes a lock or seal that is broken upon opening the chamber and that does not allow the chamber to be closed again (thereby preventing the chamber from being opened and closed prior to surgery). It should be appreciated that one or more additional mechanisms may be provided to maintain the sterility of the reactor chamber and/or to confirm that the reactor chamber has not been opened prior to surgery.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, aspects of the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A bioreactor comprising:
    vessel having side walls defining a chamber, the side walls having a first end and a second end opposed to the first end, the chamber having at least one opening that communicates with the chamber, the at least one opening defined proximate to the first end of the side walls, the chamber being configured for containing a biological object under culture conditions;
    a cover component configured for covering the at least one opening located proximate to the first end of the side walls, the cover component removably connected to the vessel;
    ports defined in the cover component, the ports configured for providing access into the chamber while the cover component is connected to the vessel to cover the at least one opening, a first elongate member opening, and a second elongate member opening; and
    a support structure comprising:
        a support base for supporting the biological object;
        a first elongate member;
        a second elongate member, wherein each of the first elongate member and the second elongate member has a first end adjustably attached to the support base, a body portion contiguous with the first end, the body section defining an elongate member midsection, the elongate member midsection of the first elongate member passing through the first elongate member opening and the elongate member midsection of the second elongate member midsection passing through the second elongate member midsection opening in the cover component, and the first and second elongate members each having a second end disposed on a side of the cover component that is external to the chamber when the cover component is joined with the vessel to cover the at least one opening, wherein the first elongate member is adjustably attached to a first side of the support base and the second elongate member is adjustably attached to the second side of the support base, wherein the second side of the support base is opposed to the first side of the support base; and
        a crossmember having a first end attached to the second end of the first elongate member and a second end attached to the first end of the second elongate member; and
    fluid conduits, the fluid conduits each having a central body member passing through respective conduit openings defined in the cover component, each fluid conduit having a first conduit end, and a second conduit end, the first conduit end terminating at a location proximate to the support base, the second conduit end opposed to the first conduit end, the second conduit end disposed on the side of the cover component that is external to the chamber when the cover component is joined with the vessel to cover the at least one opening, wherein the central body of each respective fluid conduit is positioned parallel to either the first or second elongate member,
    wherein the support structure is configured to support the biological object when the cover component is separated from the vessel and for positioning the biological object within the chamber when the cover component is joined with the vessel to cover the at least one opening, and
    wherein the support structure is telescopically inserted into the vessel such that the side walls of the vessel surround the support structure when in a use position;
    wherein first fluid conduit is attached to the at least one port such that the fluid conduit is disposed in the chamber when the cover component is joined with the vessel to cover the at least one opening, and wherein at least a portion of the fluid conduit is disposed parallel to either the first or second elongate member; and
    wherein the first fluid conduit is configured for attachment to a second fluid conduit of the biological object.

2. The bioreactor of claim 1, wherein the support base is a movable support base configured such that a user can manipulate its position relative to the chamber when the cover component is joined with the vessel to cover the at least one opening.

3. The bioreactor of claim 1, wherein the support base has a surface for supporting the biological object that, when the cover component is joined with the vessel to cover the at least one opening, is positioned along an axis substantially parallel to the opening.

4. The bioreactor of claim 1, wherein the support base has a surface for supporting the biological object that, when the cover component is joined with the vessel to cover the at least one opening, is positioned along an axis substantially perpendicular to the opening.

5. The bioreactor of claim 1, wherein the vessel, cover component and/or support structure is composed of material(s) that can sustain temperatures within a range of 120° C. to 150° C.

6. The bioreactor of claim 1, wherein the chamber is configured for containing a biological object under sterile culture conditions.

7. The bioreactor of claim 1, wherein the vessel comprises a surface circumscribing the at least one opening that is configured to interface with a surface of the cover component when the cover component is joined with the vessel to cover the at least one opening.

8. The bioreactor of claim 1, wherein the cover component is joined with the vessel to cover the at least one opening, the cover component comprising a plurality of fasteners disposed around the periphery of the cover component.

9. The bioreactor of claim 8 further comprising a biological object positioned within the chamber.

10. The bioreactor of claim 8, wherein the biological object is suspended in the chamber by the support base.

* * * * *